US006685452B2

(12) United States Patent
Christiansen et al.

(10) Patent No.: US 6,685,452 B2
(45) Date of Patent: Feb. 3, 2004

(54) IMPLANTABLE DRUG DELIVERY PUMP WITH DESICCANT HUMIDITY PROTECTION

(75) Inventors: Chris C. Christiansen, 4641 Hillvale Cir. North, Oakdale, MN (US) 55128; James M. Olsen, 10380 51st Pl. N., Plymouth, MN (US) 55442

(73) Assignees: Chris C. Christiansen, Oakdale, MN (US); James M. Olsen, Plymouth, MN (US)

( * ) Notice: Subject to any disclaimer, the term of this patent is extended or adjusted under 35 U.S.C. 154(b) by 169 days.

(21) Appl. No.: 09/925,598

(22) Filed: Aug. 9, 2001

(65) Prior Publication Data

US 2002/0161354 A1 Oct. 31, 2002

Related U.S. Application Data

(60) Provisional application No. 60/286,609, filed on Apr. 26, 2001.

(51) Int. Cl.⁷ ................................................ F04B 39/00
(52) U.S. Cl. ..................................... 417/572; 604/891.1
(58) Field of Search .......................... 417/572; 604/65, 604/66, 67, 890.1, 891.1, 892.2

(56) References Cited

U.S. PATENT DOCUMENTS

| 2,783,547 | A | * | 3/1957 | Bieger et al. ................ 34/563 |
| 3,091,550 | A | * | 5/1963 | Doying ........................ 427/387 |
| 4,576,556 | A | | 3/1986 | Thompson |
| 4,692,147 | A | | 9/1987 | Duggan ........................ 604/93 |
| 4,784,645 | A | * | 11/1988 | Fischell ..................... 604/891.1 |
| 4,978,338 | A | | 12/1990 | Melsky et al. |
| 5,814,091 | A | * | 9/1998 | Dahlberg et al. ............. 607/36 |
| 6,036,459 | A | | 3/2000 | Robinson |
| 6,146,743 | A | | 11/2000 | Haq et al. |

FOREIGN PATENT DOCUMENTS

| GB | 2190742 A | * | 11/1987 | .............. 604/891.1 |

* cited by examiner

Primary Examiner—Cheryl J. Tyler
(74) Attorney, Agent, or Firm—Banner & Witcoff, Ltd.

(57) ABSTRACT

A human body implantable drug delivery pump has a housing including at least a first shield and a second shield. The housing defines an interior within the shields. The pump further includes a fluid reservoir within the housing, a fluid conduit also within the housing from the reservoir, an outlet from the fluid conduit to the exterior of the housing, and a pump member in the housing adapted to move fluid through the fluid conduit to the outlet. The fluid in the reservoir and fluid conduit is isolated from the pump interior. The pump further has a desiccant in the pump interior, the desiccant absorbent of moisture in the pump interior, and preferably absorbent of substantially all the moisture in the pump interior. The desiccant also preferably has a moisture absorbent property dependent on temperature, being lessened at higher temperatures, the desiccant being pre-baked to improve its moisture absorbent property before being placed in the pump.

20 Claims, 4 Drawing Sheets

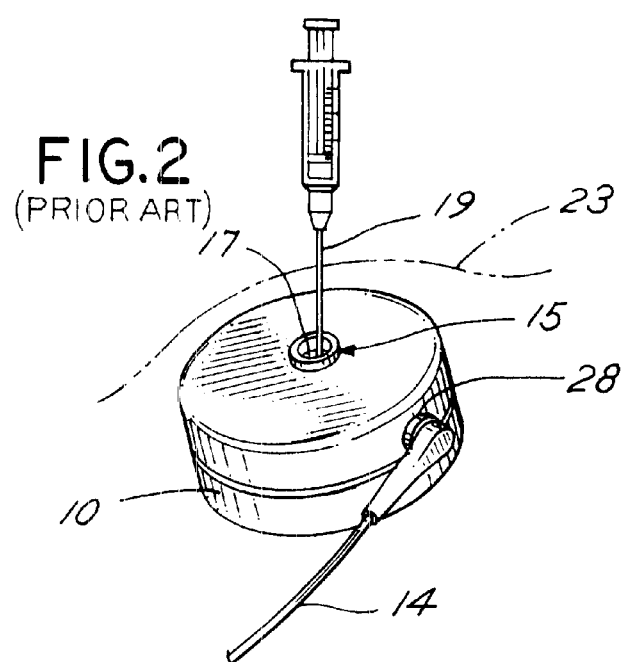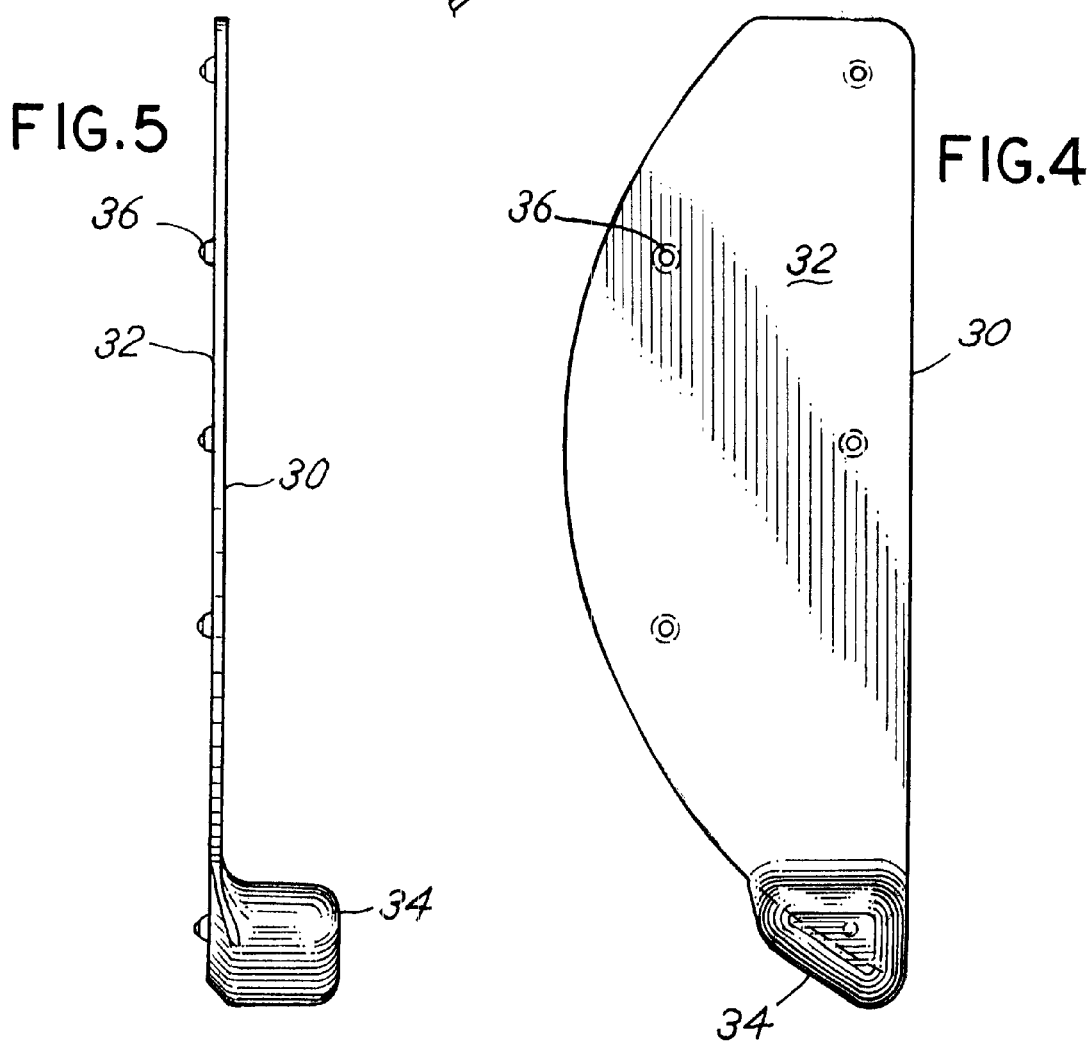

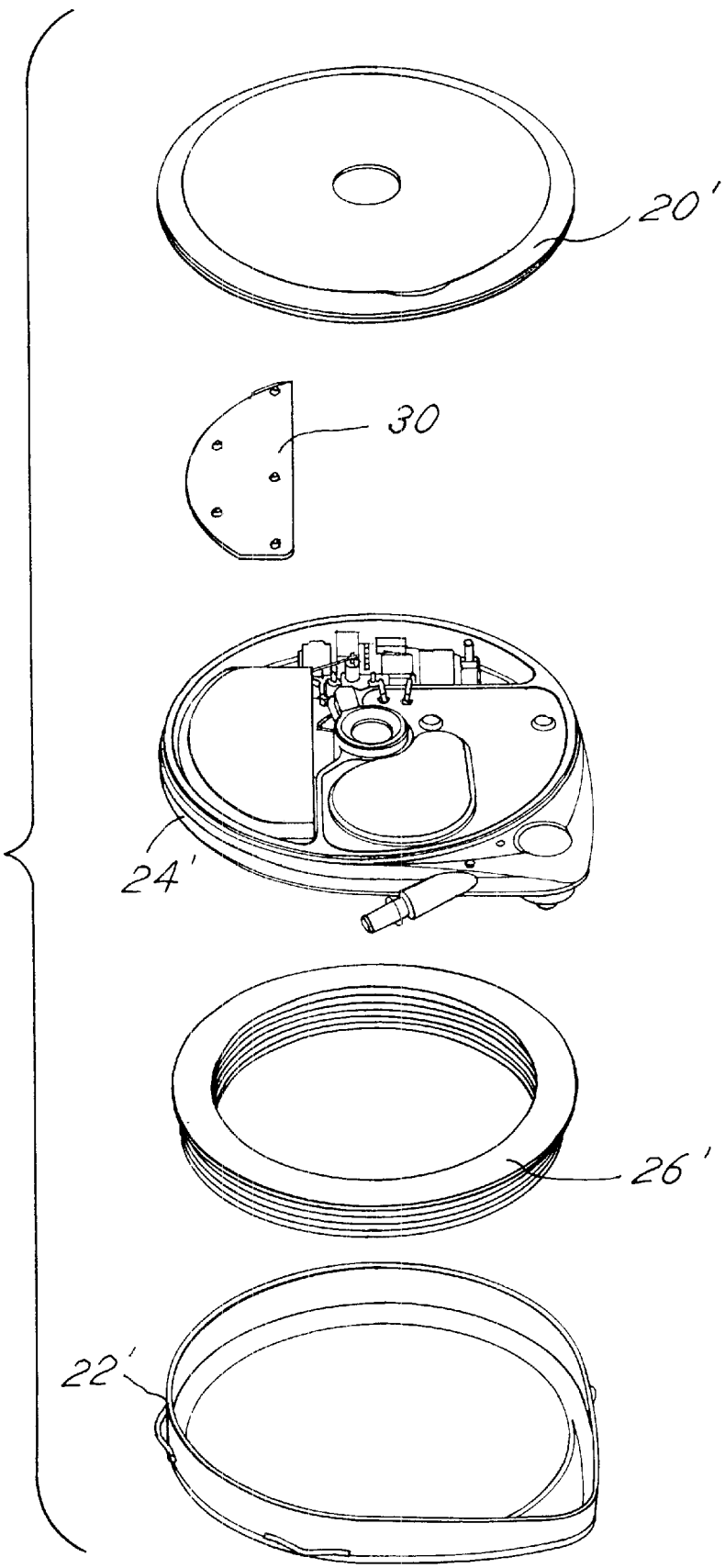

IMPLANTABLE DRUG DELIVERY PUMP WITH DESICCANT HUMIDITY PROTECTION

RELATED APPLICATION

This is a non-Provisional application claiming priority of Provisional application No. 60/286,609, filed on Apr. 26, 2001.

BACKGROUND OF THE INVENTION

This invention relates to medical devices, and more specifically, to human body implantable drug delivery pumps.

PAIN

Briefly, the brain, not the point of an injury, registers any sensation of pain. When pain is felt, it is a reaction to signals that are transmitted throughout the body. These signals are sent from the pain source, through the nerves in the spinal cord, to the brain, where they are perceived as pain. Pain can be controlled by preventing the pain signals from reaching the brain.

The origin of some pain is neuropathic, while other pain is nociceptive. Neuropathic pain is pain that is caused by damage to nerve tissue. Nociceptive pain means pain caused by an injury or disease outside the nervous system.

Acute pain (such as spraining an ankle) acts as a warning to signal harm or possible damage to tissues in the body. It prevents additional damage by alerting you to react and remove the source of pain. However, when pain lasts a long time (over six months) and is not relieved by standard medical management, it is called "chronic" pain. In chronic pain, the pain signal no longer helps, but hinders the body. Pain is recognized as a major public health problem. In the United States, it is estimated that chronic pain affects 15% to 33% of the U.S. population, or as many as 70 million people. In fact, chronic pain disables more people than cancer or heart disease and costs the American people more than both combined. Pain costs an estimated $70 billion a year in medical costs, lost working days, and workers' compensation.

ADVANCED PAIN THERAPIES

APT™ Neurostimulation ("Advanced Pain Therapy Neurostimulation") is available from Medtronic, Inc., and commonly used for neuropathic pain. APT™ Intrathecal treatment, also available from Medtronic, Inc., is commonly used for nociceptive pain.

APT™ Neurostimulation (including both spinal cord stimulation and peripheral nerve stimulation) uses a small neurostimulation system that is surgically placed under the skin to send mild electrical impulses to the spinal cord. The electrical impulses are delivered through a lead (a special medical wire) that is also surgically placed. These electrical impulses block the signal of pain from reaching the brain. Peripheral nerve stimulation works in the same way, but the lead is placed on the specific nerve that is causing pain rather than the spinal cord.

APT™ Intrathecal uses a small pump that is surgically placed under the skin of the abdomen to deliver medication directly into the intrathecal space (where fluid flows around the spinal cord). The medication is delivered through a small tube called a catheter that is also surgically placed. The spinal cord is like a highway for pain signals on their way to the brain, where the feeling of pain is experienced by the body. Because the medication goes directly to the site of action in the spinal cord, where pain signals travel, APT™ Intrathecal offers many people significant pain control with much lower doses of medication than would be required by oral medications (pills). This helps minimize the side effects that often accompany other treatments.

A doctor can do a screening test to see if APT™ Intrathecal will relieve pain, before the patient commits to the therapy. In addition, APT™ Intrathecal is non-destructive and reversible. Typically, people who have success with APT™ Intrathecal experience greater than 50% reduction in their pain and improved ability to go about activities of daily living.

The SynchroMed® Infusion System is a fully implantable, programmable APT™ Intrathecal system available from Medtronic. The SynchroMed® Infusion System has two parts that are both placed in the body during a surgical procedure: the catheter and the pump. The catheter is a small, soft tube. One end is connected to the catheter port of the pump, and the other end is placed in the intrathecal space (where fluid flows around the spinal cord). The pump is a round metal device that stores and releases prescribed amounts of medication directly into the intrathecal space. It is about one inch (2.5 cm) thick, three inches (8.5 cm) in diameter, and weighs about six ounces (205 g). It is made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SynchroMed® pump automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription is stored in the pump's memory. The doctor can easily review this information by using the programmer. The programmer communicates with the pump by radio signals that allow the doctor to tell how the pump is operating at any given time. The doctor also can use the programmer to change your medication dosage.

CURRENT TECHNIQUE FOR HUMIDITY PROTECTION

As indicated, an APT™ Intrathecal pump is a sophisticated electromechanical device. In addition to its reservoir, fill port, and other mechanical components, the device includes microelectronics in an electronic chamber. Implantation of an APT™ Intrathecal pump is also a significant life event. Given the electronics in the units and the significance of implantation, long-term excellence in the performance of the units is highly desirable. Unfortunately, one common failure mode (way things fail) for implantable device electronics is corrosion of conduction pathways, or short circuiting of the pathways, caused by the presence of water vapor and salts. The short circuiting of the pathways often occurs from dendrites which form between circuits which are at different voltage potentials, when in the presence of ionic vapors. Plastic components in the electronics (e.g., chip carriers), absorb trace amounts of water vapor in normal air, and these vapors can leave the plastics after implantation, risking corrosion.

Consistently, the electronics of the devices are protected. They are protected against liquids, and against humidity. Liquid protection, by surrounding the electronics in a hermetic enclosure, prevents entry of fluids from the human body or drugs from the drug pathway. Humidity protection provides for a dry environment for the internal electronic components. A dry interior promotes long life and accuracy in the performance of the electronic components.

In current device manufacture, a last or near-last step of manufacture is the humidity protection step. The device is fully assembled, with only a pinhole called a "tig" hole remaining as an opening to the interior. The unit is then "baked" by bringing it to a temperature of about 100 degrees Fahrenheit (37 degrees C.) while a vacuum is created in the heating chamber or "oven". The air inside the unit is pulled by the vacuum through the tig hole, bringing internal moisture, including moisture previously absorbed in plastic components, out with it. Typically, the tig hole is so small that the time necessary to pull the air from the unit is a day to two days. The external vacuum is then reduced and in a short time, the baked unit is "backfilled" with helium, meaning the vacuum inside the unit is filled with helium, also through the tig hole. Within the short time available, the tig hole is then welded closed.

This vacuum bake time can be a significant time constraint for assembling the implantable pump.

SUMMARY OF THE INVENTION

A primary object of the invention is to substantially advance the construction of human body implantable drug delivery pumps.

Another primary object is to substantially advance the manufacturing methods employed for manufacturing such pumps.

Another primary object is to minimize the consumption of time required by the current technique for humidity protection, and the complication of the rigors of time, temperature, vacuum, and location of its use.

Another primary object is to imbue the human body implantable drug delivery pump with structure eliminative of the current technique for humidity protection; that is, to provide a construction of the unit that permits assembly without use of the current technique for humidity protection.

Another object is to imbue the pump with structure that allows the reduction of a hermetic barrier between the electronics area and the motor area; that is, to provide a construction that works with a hermetic seal of the electronics area and motor area together, assuming the motor system has an impermeable barrier tubing that contains the drug being delivered.

Other primary objects include providing a pump structure eliminative and potentially eliminative of the unit baking and its use and complication, eliminative and potentially eliminative of the vacuum creation and its use and complication, and eliminative and potentially eliminative of the tig hole and its use and complication.

In a first aspect, then, the invention includes an improvement in a human body implantable drug delivery pump that comprises a housing including at least a first shield and a second shield. The housing defines an interior within the shields. The pump further includes a fluid reservoir within the housing, a fluid conduit also within the housing from the reservoir, an outlet from the fluid conduit to the exterior of the housing, and a pump member in the housing adapted to move fluid through the fluid conduit to the outlet. The fluid in the reservoir and fluid conduit is isolated from the pump interior. The pump further comprises a desiccant in the pump interior, the desiccant absorbent of moisture in the pump interior, and preferably absorbent of substantially all the moisture in the pump interior.

In another principal aspect, the invention is directed specifically to improvement in a human body implantable drug delivery pump of the type described in which the desiccant has a moisture absorbent property dependent on temperature, being lessened at higher temperatures, the desiccant being pre-heated to improve its moisture absorbent property before being placed in the pump. The desiccant is also further absorbent of moisture, whereby the desiccant may be placed within the housing during final assembly of the pump when the pump housing is not completely sealed, and the desiccant is absorbent during a time period of final assembly, and remains absorbent of substantially all the moisture within the housing after complete sealing of the housing. Most preferably, the desiccant is molded to fit free space within the housing, and the desiccant comprises a mixture of liquid silicon rubber and aluminum oxide.

These and other objects, aspects and advantages of the invention and its preferred embodiments are best understood by a complete reading of the detailed description of the preferred embodiment of the invention, which follows a brief description of the accompanying drawing.

BRIEF DESCRIPTION OF THE DRAWING

A drawing accompanies this specification, and includes a variety of figures. They are each briefly described as follows:

FIG. 2 is a pictorial view of the pump of FIG. 1 as implanted, with human skin in phantom;

FIG. 4 is a plan view of a desiccant body of the invention;

FIG. 5 is a side elevation view of the desiccant body; and

FIG. 6 is an exploded view similar to FIG. 3 of a pump with dessicant body. FIGS. 2 and 3 are taken from U.S. Pat. No. 4,692,147 for economy. As will become apparent, the specific internal and external construction of the pump associated with the invention is not particularly significant to the application of the invention. Except as claimed, the detail of the pump is not considered critical or limiting of the claims made to the invention.

DETAILED DESCRIPTION OF THE PREFERRED EMBODIMENT

Figure 1:
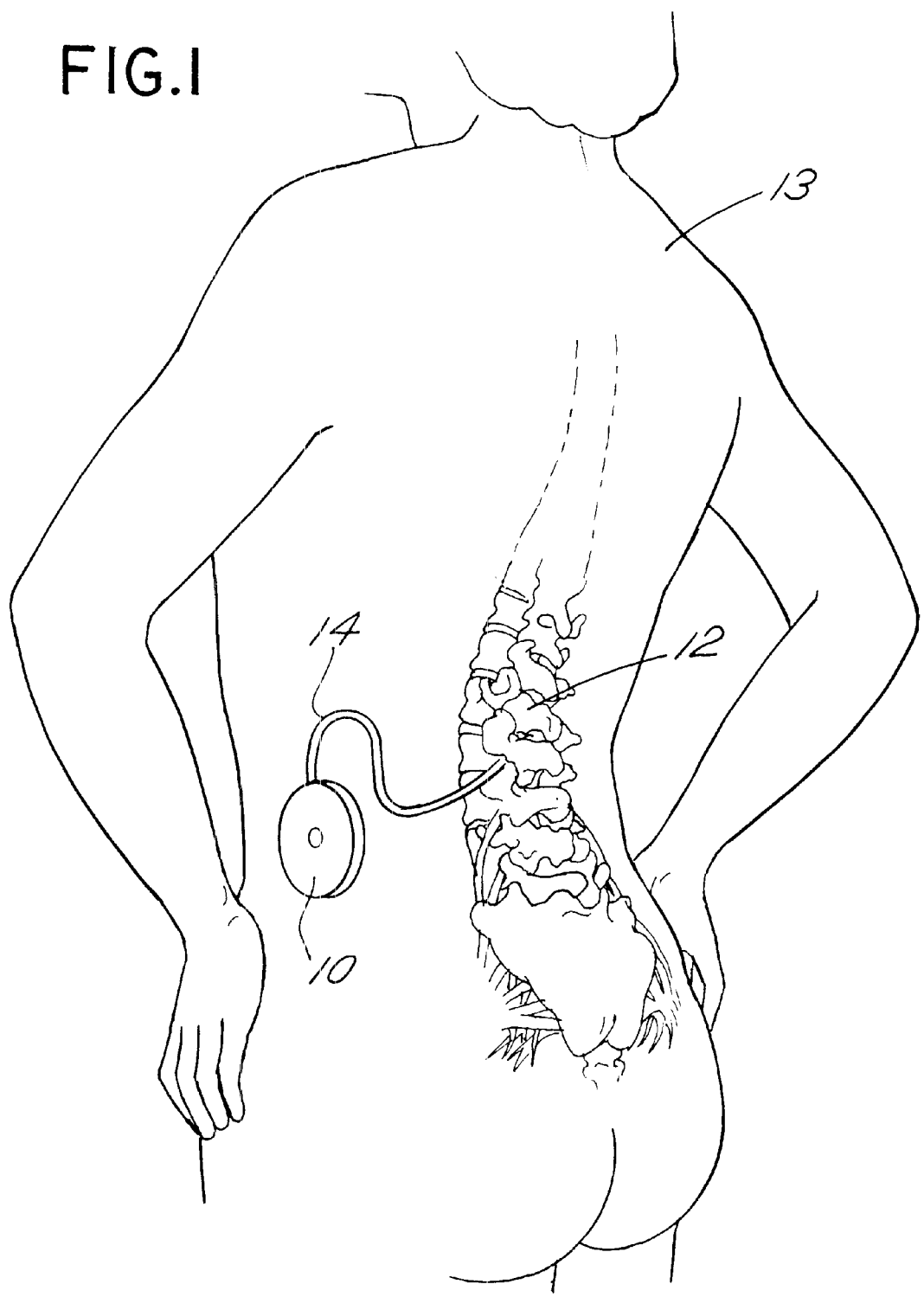
FIG. 1 is a diagrammatic view of a human patient in which a representative form of human implantable drug delivery pump is implanted for pain treatment.

As in FIG. 1, APT™ Intrathecal in the form of the SynchroMed® Infusion System from Medtronic, Inc. uses a small pump 10 that is surgically placed under the skin of the abdomen of a human patient 13 to deliver medication directly into the intrathecal space in the spinal column 12 (where fluid flows around the spinal cord). The medication is delivered through a small tube 14 called a catheter that is also surgically placed. APT Intrathecal treatment offers many people significant pain control with much lower doses of medication than would be required by oral medications (pills). The pump 10 as shown is a round metal—titanium—device, in this case about one inch (2.5 cm) thick, three inches (8.5 cm) in diameter. It weighs about six ounces (205 g). Inside it has a reservoir, i.e., a space that holds medication.

Turning to FIG. 2, a fill port 15 is in a raised center portion or septum 17 of the pump 10 through which the pump is refilled. The doctor or a nurse inserts a needle 19 through the patient's skin 23 and through the fill port to fill the pump. Some pumps have a side catheter access port that allows the doctor to inject other medications or sterile solutions directly into the catheter, bypassing the pump.

The SynchroMed® pump 10 automatically delivers a controlled amount of medication through the catheter 14 to the intrathecal space around the spinal cord, where it is most effective. The exact dosage, rate and timing are prescribed by the treating physician. These factors are entered in the internal electronic controls of the pump using a programmer, not shown, which is an external computer-like device that controls the pump's internal memory. Information about the patient's prescription is then stored in the pump's memory. The programmer communicates with the pump by radio signals.

Much additional information about APT™ Intrathecal, specifically the SynchroMed® Infusion System, and most specifically the advantages of the available medical treatments are available from implanting physicians, from Medtronic, Inc., and from the medical and scientific literature. All those who are potential candidates for treatment are encouraged to seek reliable medical information from authoritative sources. For the purpose of this detailed description of the invention, the focus will be on the invention in its desiccant and the invented manufacturing method. Broader information on drug delivery pumps is also available in the patent literature, as for example in U.S. Pat. No. 6,036,459 to Robinson issued Mar. 14, 2000, U.S. Pat. No. 4,692,147 issued to Duggan Sep. 8, 1987, U.S. Pat. No. 4,576,556 issued Mar. 18, 1986 to Thompson, and U.S. Pat. No. 4,978,338 issued to Melsky Dec. 18, 1990, and the prior art they cite.

Attention is also directed to U.S. Pat. No. 6,146,743. This patent discusses barrier metalization in ceramic substrates for implantable medical devices. The patent is intended for multi-layer ceramic substrates and the processing necessary to protect the substrate and hybrid from moisture. A desiccant shield or cover 80 is in FIG. 14. The electronics packing for the pump 10 does not use ceramic, but uses printed wiring board (PWB) technology. The substrate and subsequent components available for surface mounting for PWB are mainly plastic packages subject to water absorption. The high density nature of the electronics (i.e., pitch <0.025 inches) makes it imperative that water vapor and salts are controlled as distance between electrical pathways continues to shrink.

Figure 3:
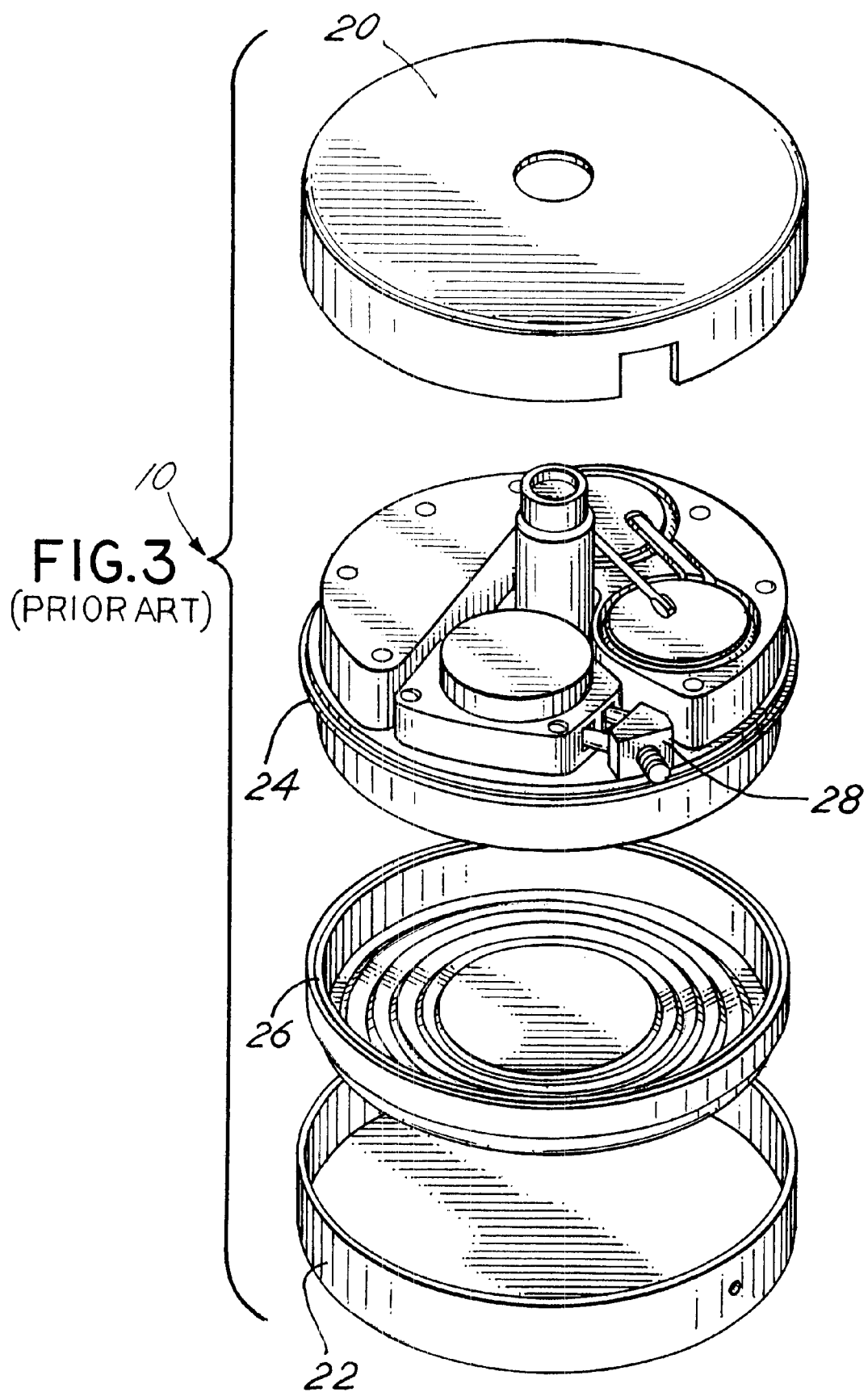
FIG. 3 is an exploded view of the representative pump.

Referring to FIG. 3, two shields or shells 20, 22 form the housing of the pump 10, and define its exterior and interior. The shields 20, 22 come together about a center plate or bulkhead 24. The lower portion of the pump, between the bulkhead 24 and lower shield 22, includes two sealed areas: a reservoir chamber, and an outer chamber. A bellows 26 separates and defines the two chambers. The reservoir holds medication or infusate introduced through the fill port 15, and the bellows 26 expands and contracts in response to the pressure applied externally to the bellows by a two-phase fluid in the outer chamber, maintaining pressure in the reservoir.

A fluid conduit extends through a flexible tube from the reservoir, to an outlet or catheter port 28 extending from the exterior of the pump housing. As stated in the Duggan U.S. Pat. No. 4,692,147 at column 3, lines 17–38, incorporated by reference, the conduit extends through a pump member in the form of a motor-driven peristaltic roller pump, where rollers move or press the fluid or infusate forward toward the outlet when activated.

As stated in Duggan at column 3, lines 11–12, incorporated by reference, the pump 10 further includes an electronic circuit module driven by suitable capacitive energy storage units. The circuit module provides instruction to the roller pump, and includes a microprocessor, memory, and such other electronic componentry as necessary to have the pump function as indicated above.

As appropriate to implantation in the human body, the pump 10 is hermetically sealed as the pump is in its final manufactured form. To achieve the sealing, the shields are welded to the center plate. The welds are tested to withstand internal and external pressures, pull forces, and leakage.

Referring to FIGS. 4, 5 and 6, in contrast with the above-described "Current Technique for Humidity Protection," a desiccant body 30 is formed to fit in free space within the pump 10'. The body 30 fits between the shield 20' and the bulkhead 24'. The pump also includes its bellows 26' and second shield 22'. Primarily to fit within available space, the body 30 includes a thin plate section 32 and an integral knob section 34. Four protuberances or bumps such as the one designated 36 are spaced across the plate section 32. These abut the shield 20' and the plate section 32 abuts underlying structure(s) to hold the body 30 in place under the compression of the fit between the shield 20' and the bulkhead 24'. The protuberances also expose the upper surface of the plate section 32 to gases within the pump 10', allowing more rapid moisture absorption as will be explained.

The body 30 is formed of a high percentage of aluminum oxide (AlO) and a high percentage of liquid silicone rubber (LSR). Most preferably, the percentages are 40–50%±2% aluminum oxide by weight and 50–60%±2% LSR by weight. The AlO percentage is measured after exposure to air for 24 hours minimum, while the AlO is in powder condition in a layer no thicker than 0.5 inch (12.7 mm). The AlO powder is mixed in the LSR, and the mixture molded to the shape shown. Care is taken to assure the part is not exposed to heptane, alcohol or other solvents other than water. The resulting body 30 is moisture absorbent.

The desiccant body 30 has a moisture capacity based on its composition and size. As most preferred, the capacity of the body is sufficient, once moisture has been baked out, to absorb moisture in the interior components of the pump above the bulkhead 24', once the pump 10' is backfilled with helium and welded sealed, to a desired or predetermined level of dryness, and most preferably to substantially complete dryness. The pumps 10' will have been assembled in clean rooms, where relative humidity is typically specified in the range of 45% to 60%, and the electronic and perhaps other components will have absorbed moisture. Also as most preferred, the body, once baked, has sufficient moisture capacity to absorb moisture as indicated, and also to absorb moisture in advance of sealing of the pumps 10', during a time period of exposure of the desiccant body to the atmosphere of the clean room during final assembly of the pump and before the pump is welded. As most preferred, the capacity of the body 30 is sufficient for ninety minutes of assembly time in the clean room and substantially complete dryness of the pump interior.

To assure the body 30 is sized properly for the unique circumstances addressed by others of skill in the art, test bodies can be formed and installed under expected working conditions. Test pumps may be sealed. The devices may then be warmed, to drive deeply embedded moisture into the gases in the pumps, and after an appropriate time period such as two days, the pumps may be pierced. The gases may be tested for moisture content, and the desiccant body composition and size validated, or varied for further testing.

Thus, as can be fathomed at this point, the method of manufacturing a human body implantable drug delivery device with the desiccant body 30 includes pre-baking the body. The desiccant of the body has a moisture absorption capacity depend on temperature that is improved on baking. Baking drives moisture from the body.

The pump 10' in contrast, does not need to be baked. It also need not be placed in a vacuum. The desiccant body allows substrate, usually FR-4, components and metal components to be assembled without vacuum baking or a humidity controlled environment. On arrival at the final stage of assembly, the stage including sealing by welding, the pump may be maintained in clean room conditions, at room temperature, room humidity, and room pressure. The desiccant body may be placed in the unit, and final assembly accomplished while the desiccant body is exposed to clean room atmosphere. The assembly time period should extend for no longer than the time for which the body has been validated for exposure, by testing for composition and size, but the assembly may occur with the body exposed. In completion of final assembly, the pump may be helium filled and sealed by welding. The desiccant of the body will remain absorbent within its tested capacity, and if composition and size has been well chose, the desiccant will absorb substantially all the moisture in the electronic chamber of the pump.

For this specification, the term "absorb moisture" means to absorb some moisture, whether all moisture is absorbed, a significant portion of moisture is absorbed, or only some moisture is absorbed. "Absorb" means to take in, for a significant period of time. Other terms shall have the meaning ascribed to those terms by persons of ordinary skill in the art.

The preferred embodiments of the invention, and the invention itself, are now described in such full, clear, concise and exact terms as to enable a person of ordinary skill in the art to make and use the invention. To particularly point and distinctly claim the subject matters regarded as invention, the following claims conclude this specification. To the extent variations from the preferred embodiments fall within the limits of the claims, they are considered to be part of the invention, and claimed.

What is claimed is:

1. A human body implantable drug delivery pump comprising a housing of assembled components including electronics, the pump further comprising a desiccant located interiorly to the housing and in the same environment as the electronics, whereby the desiccant absorbs moisture within the environment of the electronics.

2. A human body implantable drug delivery pump as in claim 1 in which the desiccant is absorbent of moisture within the housing to a desired level.

3. A human body implantable drug delivery pump as in claim 2, the desiccant absorbent of substantially all the moisture in the pump interior.

4. A human body implantable drug delivery pump as in claim 2 in which the desiccant is further absorbent of moisture, whereby the desiccant may be placed within the housing during final assembly of the pump when the pump housing is not completely sealed, and the desiccant is absorbent during a time period of final assembly, and remains absorbent of substantially all the moisture within the housing after complete sealing of the housing.

5. A human body implantable drug delivery pump as in claim 2, the desiccant absorbent of substantially all the moisture in the pump interior.

6. A human body implantable drug delivery pump as in claim 1 in which the moisture absorbent property of the desiccant is dependent on temperature, being lessened at higher temperatures, the desiccant being pre-heated to improve its moisture absorbent property.

7. A human body implantable drug delivery pump as in claim 1 in which the desiccant is molded to fit free space within the housing.

8. A human body implantable drug delivery pump as in claim 1 in which the desiccant comprises liquid silicon rubber.

9. A human body implantable drug delivery pump as in claim 1 in which the desiccant comprises aluminum oxide.

10. A human body implantable drug delivery pump as in claim 1, in which the desiccant is absorbent of substantially all the moisture in the pump interior, in which the moisture absorbent property of the desiccant is dependent on temperature, being lessened at higher temperatures, the desiccant being pre-heated to improve its moisture absorbent property, in which the desiccant is further absorbent of moisture, whereby the desiccant may be placed within the housing during final assembly of the pump when the pump housing is not completely sealed, and the desiccant is absorbent during a time period of final assembly, and remains absorbent of substantially all the moisture within the housing after complete sealing of the housing, and in which the desiccant comprises liquid silicon rubber and aluminum oxide.

11. A human body implantable drug delivery pump, the pump comprising a housing including at least a first shield and a second shield, the housing defining an interior within the shields, the pump further including electronics and a fluid reservoir within the housing, a fluid conduit also within the housing from the reservoir, an outlet from the fluid conduit to the exterior of the housing, and a pump member in the housing adapted to move fluid through the fluid conduit to the outlet, the fluid in the reservoir and the fluid conduit isolated from the pump interior, the pump further comprising a desiccant in the pump interior and in the same environment as the electronics, the desiccant absorbent of moisture in the pump interior.

12. A human body implantable drug delivery pump as in claim 11 in which the desiccant is absorbent of moisture within the pump interior to a desired level.

13. A human body implantable drug delivery pump as in claim 11 in which the moisture absorbent property of the desiccant is dependent on temperature, being lessened at higher temperatures, the desiccant being pre-heated to improve its moisture absorbent property.

14. A human body implantable drug delivery pump as in claim 11 in which the desiccant is further absorbent of moisture, whereby the desiccant may be placed within the housing during final assembly of the pump when the pump housing is not completely sealed, and the desiccant is absorbent during a time period of final assembly, and remains absorbent of substantially all the moisture within the pump interior after complete sealing of the housing.

15. A human body implantable drug delivery pump as in claim 11 in which the desiccant is molded to fit free space within the pump interior.

16. A human body implantable drug delivery pump as in claim 11 in which the desiccant comprises liquid silicon rubber.

17. A human body implantable drug delivery pump as in claim 11 in which the desiccant comprises aluminum oxide.

18. A human body implantable drug delivery pump as in claim 11 in which the desiccant is absorbent of substantially all the moisture within the pump interior, in which the moisture absorbent property of the desiccant is dependent on temperature, being lessened at higher temperatures, the desiccant being pre-baked to improve its moisture absorbent property, in which the desiccant is further absorbent of moisture, whereby the desiccant may be placed within the housing during final assembly of the pump when the pump housing is not completely sealed, and the desiccant is absorbent during a time period of final assembly, and remains absorbent of substantially all the moisture within the housing after complete sealing of the housing, in which the desiccant is molded to fit free space within the housing, and in which the desiccant comprises liquid silicon rubber and aluminum oxide.

19. A human body implantable drug delivery pump, the pump comprising a housing including at least a first shield and a second shield, the housing defining an interior within the shields, the pump further including a fluid reservoir within the housing and electronics exposed to the first shield and non-exposed to the second shield, a fluid conduit also within the housing from the reservoir, an outlet from the fluid conduit to the exterior of the housing, and a pump member in the housing adapted to move fluid through the fluid conduit to the outlet, the fluid in the reservoir and fluid conduit isolated from the pump interior, a desiccant being absorbent of substantially all the moisture within an environment between the first shield and the electronics, the desiccant having a moisture absorbent property dependent on temperature, being improved after being raised to higher temperatures, the desiccant being pre-baked to improve its moisture absorbent property before being placed in the pump, the desiccant being further absorbent of moisture, whereby the desiccant is placed within the environment between the first shield and the electronics during final assembly of the pump when the pump housing is not completely sealed, and the desiccant is absorbent during a time period of final assembly, and remains absorbent of substantially all the moisture within the environment between the first shield and the electronics after complete sealing of the housing, the desiccant being molded to fit free space within the environment between the first shield and the electronics, and the desiccant comprising liquid silicon rubber and aluminum oxide.

20. A method of manufacturing a human body implantable drug delivery pump, comprising forming the pump as having a housing including at least a first shield and a second shield, the housing defining an interior within the shields, the pump further including a fluid reservoir within the housing, a fluid conduit also within the housing from the reservoir, an outlet from the fluid conduit to the exterior of the housing, and a pump member in the housing adapted to move fluid through the fluid conduit to the outlet, the fluid in the reservoir and fluid conduit isolated from the pump interior, the method also comprising inserting in the pump interior a desiccant and then sealing the housing in a final assembly step, the desiccant being one that is absorbent of substantially all the moisture within the pump interior, the desiccant having a moisture absorbent property dependent on temperature, being improved after being raised to higher temperatures, the desiccant being pre-baked to improve its moisture absorbent property before being placed in the pump, the desiccant also being formed in type and size to be further absorbent of moisture, whereby the desiccant may be placed within the housing during final assembly of the pump when the pump housing is not completely sealed, and the desiccant is absorbent during a time period of final assembly, and remains absorbent of substantially all the moisture within the housing after complete sealing of the housing, the desiccant further being molded to fit free space within the housing, and the desiccant comprising liquid silicon rubber and aluminum oxide.

* * * * *

UNITED STATES PATENT AND TRADEMARK OFFICE
CERTIFICATE OF CORRECTION

PATENT NO. : 6,685,452 B2
APPLICATION NO. : 09/925598
DATED : February 3, 2004
INVENTOR(S) : Christiansen et al.

It is certified that error appears in the above-identified patent and that said Letters Patent is hereby corrected as shown below:

Title Page, Section (73) Assignees: "Chris C. Christiansen, Oakdale, MN (US); James M. Olsen, Plymouth, MN (US) should be -- Medtronic, Inc., Minneapolis, MN (US) --

Signed and Sealed this

Twenty-second Day of August, 2006

JON W. DUDAS
*Director of the United States Patent and Trademark Office*